United States Patent [19]
Weil et al.

[11] Patent Number: 6,071,237
[45] Date of Patent: Jun. 6, 2000

[54] DEVICE AND METHOD FOR ASSESSING PERFUSION FAILURE IN A PATIENT DURING ENDOTRACHEAL INTUBATION

[75] Inventors: Max Harry Weil, Northbrook, Ill.; Wanchun Tang, Palm Desert; Jose Bisera, Camarillo, both of Calif.

[73] Assignee: Institute of Critical Care Medicine, Palm Springs, Calif.

[21] Appl. No.: 09/252,633

[22] Filed: Feb. 19, 1999

[51] Int. Cl.[7] .............................. A61B 5/00; A61M 16/04
[52] U.S. Cl. ...................... 600/309; 600/342; 128/202.22
[58] Field of Search ..................................... 600/309, 310, 600/311, 322, 341, 342, 343, 364; 128/200.26, 202.22, 205.23, 207.15

[56] References Cited

U.S. PATENT DOCUMENTS

| | | |
|---|---|---|
| 3,905,889 | 9/1975 | Macur et al. . |
| 4,016,863 | 4/1977 | Brantigan . |
| 4,381,011 | 4/1983 | Somers, 3rd . |
| 4,503,859 | 3/1985 | Petty et al. . |
| 4,535,786 | 8/1985 | Kater . |
| 4,577,109 | 3/1986 | Hirschfeld . |
| 4,632,119 | 12/1986 | Reichstein . |
| 4,643,192 | 2/1987 | Fiddian-Green . |
| 4,729,824 | 3/1988 | Giner . |
| 4,785,814 | 11/1988 | Kane . |
| 4,789,453 | 12/1988 | Eberhard et al. . |
| 4,816,131 | 3/1989 | Bomsztyk . |
| 4,833,091 | 5/1989 | Leader et al. . |
| 4,834,101 | 5/1989 | Collison et al. . |
| 4,842,783 | 6/1989 | Blaylock . |
| 4,890,619 | 1/1990 | Hatschek . |
| 4,892,383 | 1/1990 | Klainer et al. . |
| 4,919,891 | 4/1990 | Yafuso et al. . |
| 4,981,470 | 1/1991 | Bombeck, IV . |
| 5,005,573 | 4/1991 | Buchanan ................................ 600/338 |
| 5,006,314 | 4/1991 | Gourley et al. . |

(List continued on next page.)

FOREIGN PATENT DOCUMENTS

WO 94/23645   10/1994   WIPO .

OTHER PUBLICATIONS

Jin et al. (1997), "End–Tidal $PCO_2$ Serves as an Indicator of Cardiac Output During Experimental Septic Shock," *Crit. Care Med.* 25(1):A122 (Abstract).

Nakagawa et al. (1977), "Sublingual Capnometry for Quantitation of the Severity of Hemorrhagic Shock," *Shock* 7:14 (Abstract).

Nakagawa et al. (1997), "$ETCO_2$ as Non–Invasive Indicator of Cardiac Output During Hemorrhagic Shock," *Crit. Care Med.* 25(1):A132 (Abstract).

Nakagawa et al. (1977), "Sublingual Capnography as an Indicator of Perfusion Failure In Human Patients," *Chest* 112:4S (Abstract).

Nakagawa et al. (1998), "Comparison of Sublingual Capnometry with Gastric Capnometry and Lactate as Indicators of the Severity of Hemorrhagic Shock," *Crit. Care Med.* 26(1):A44 (Abstract).

Ogino et al. (1994), "Reflectance Pulse Oximeter Measuring Central SaO2 From Mouth," Proceedings of the Annual International Conference of the IEEE Engineering in Medicine and Biology Society, Baltimore, 2(16):914–915.

*Primary Examiner*—Eric F. Winakur
*Attorney, Agent, or Firm*—Dianne E. Reed; Reed & Associates

[57] ABSTRACT

A device and method are provided for assessing impairment of blood circulation in a patient, such as that in perfusion failure, wherein the patient requires mechanical ventilatory support. The invention involves measurement of $PCO_2$ (partial pressure of carbon dioxide) within the lower respiratory tract of the patient, using a device that includes an endotracheal breathing tube for introducing air from an air supply pump into a patient's lungs, wherein a carbon dioxide sensor is provided as an integral part of that device, i.e., is physically connected to the endotracheal breathing tube in a manner that allows for $PCO_2$ measurement along the sidewall of the patient's trachea.

43 Claims, 3 Drawing Sheets

U.S. PATENT DOCUMENTS

| | | |
|---|---|---|
| 5,098,659 | 3/1992 | Yim et al. . |
| 5,105,812 | 4/1992 | Corman . |
| 5,117,827 | 6/1992 | Stuebe et al. . |
| 5,158,083 | 10/1992 | Sacristan et al. . |
| 5,174,290 | 12/1992 | Fiddian-Green . |
| 5,193,544 | 3/1993 | Jaffe ......................................... 600/323 |
| 5,280,548 | 1/1994 | Atwater et al. . |
| 5,329,922 | 7/1994 | Atlee, III . |
| 5,330,718 | 7/1994 | Hui et al. . |
| 5,341,803 | 8/1994 | Goldberg et al. . |
| 5,368,027 | 11/1994 | Lübbers et al. . |
| 5,408,999 | 4/1995 | Singh et al. . |
| 5,411,022 | 5/1995 | McCue et al. . |
| 5,423,320 | 6/1995 | Salzman et al. . |
| 5,453,248 | 9/1995 | Olstein . |
| 5,456,251 | 10/1995 | Fiddian-Green . |
| 5,479,923 | 1/1996 | Rantala . |
| 5,579,763 | 12/1996 | Weil et al. . |
| 5,596,988 | 1/1997 | Markle et al. . |
| 5,631,340 | 5/1997 | Olstein . |
| 5,714,121 | 2/1998 | Alderete et al. . |
| 5,788,631 | 8/1998 | Fiddian-Green . |

OTHER PUBLICATIONS

Peterson et al. (1984), "Fiber Optic Sensors for Biomedical Applications," *Science* 224(4645):123–127.

Sato et al. (1997), "Esophageal and Gastric $PCO_2$ Both Serve as Quantitative Indicators of Organ Blood Flow During Hemorrhagic Shock," *Crit. Care Med.* 25(1):A37 (Abstract).

Sato et al. (1997), "Esophageal $PCO_2$ as a Monitor of Perfusion Failure During Hemorrhagic Shock," *J. Appl. Physiol.* 82(2):558–562.

Seitz (1984), "Chemical Sensors Based on Fiber Optics," *Anal. Chem.* 56(1):16A–34A.

Tang et al. (1998), "Myocardial Preservation During Cardiopulmonary Resuscitation," *Curr. Opin. Crit. Care* 4:155–160.

Vurek et al. (1983), "A Fiber Optic $PCO_2$ Sensor," *Annals Biomed. Engineer.* 11:499–510.

Weil (1998), "The Assault on the Swan–Ganz Catheter," *Chest* 113:1379–1386(1998) (Invited Publication).

Xie et al. (1997), "Sublingual Capnometry for Quantitation of the Severity of Septic Shock," *Shock* 7:13–14 (Abstract).

DEVICE AND METHOD FOR ASSESSING PERFUSION FAILURE IN A PATIENT DURING ENDOTRACHEAL INTUBATION

TECHNICAL FIELD

The present invention relates generally to methods and devices for assessing perfusion failure in a patient. More particularly, the invention relates to assessment of perfusion failure in a patient by measuring the localized partial pressure of carbon dioxide at an endotracheal site.

BACKGROUND ART

Very low blood flow, or low "systemic perfusion," is typically due to low aortic pressure and can be caused by a number of factors, including hemorrhage, sepsis and cardiac arrest. When there is a reduced flow of blood from the heart, the body directs a higher portion of blood to critical organs, such as the brain, which will not survive long without a continuous supply of blood, while restricting the flow to less critical organs, such as the stomach and intestines, whose survival is not as threatened by a temporary large reduction in blood flow. Physicians commonly take advantage of this phenomenon by taking measurements in the stomach and intestine to assess perfusion failure.

Assessment of $CO_2$ concentration in the less critical organs, i.e., those organs to which blood flow is reduced during perfusion failure, is useful in perfusion assessment. Carbon dioxide production, which is associated with metabolism, continues even during low blood flow. Because $CO_2$ is not rapidly carried away during low blood flow, the concentration of $CO_2$ increases, which in turn results in a decrease in pH and an increase in partial pressure of $CO_2$ ($PCO_2$) in the less critical organs. Therefore, perfusion failure is commonly assessed by measuring pH or $PCO_2$ at these sites, especially in the stomach and intestines. For examples of catheters used to assess pH or $PCO_2$ in the stomach or intestines, see, e.g., U.S. Pat. No. 3,905,889 to Macur, U.S. Pat. No. 4,016,863 Brantigan, U.S. Pat. No. 4,632,119 to Reichstein, U.S. Pat. No. 4,643,192 to Fiddian-Green, U.S. Pat. No. 4,981,470 to Bombeck, IV, U.S. Pat. No. 5,105,812 to Corman, U.S. Pat. No. 5,117,827 to Stuebe et al. U.S. Pat. No. 5,174,290 to Fiddian-Green, U.S. Pat. No. 5,341,803 to Goldberg, U.S. Pat. No. 5,411,022 to McCue, U.S. Pat. No. 5,423,320 to Salzman et al., U.S. Pat. No. 5,456,251 to Fiddian-Green, and U.S. Pat. No. 5,788,631 to Fiddian-Green et al.

The measurement of $PCO_2$ to determine the extent of perfusion failure has commonly been done by threading a catheter through the nasal passage, past the epiglottis, through the esophagus, past the esophageal sphincter, and into the stomach, and sometimes through the stomach and into the intestines. Alternatively, measurement has been conducted in the colon, with a catheter being threaded through the anus. These procedures are obviously quite invasive and can cause harm and discomfort to a patient. Moreover, insertion of the catheter in this manner is also complex and time-consuming.

In U.S. Pat. No. 5,579,763 to Weil et al., applicants described the introduction of a catheter with a carbon dioxide sensor through the nasal or oral passage, past the epiglottis, and into the esophagus so that the catheter and sensor lay within the esophagus. This method can be used to accurately assess perfusion failure by measuring $PCO_2$ in the patient's esophagus of a patient, rather than in the stomach and/or intestine. Tests showed that measurements of $PCO_2$ in the esophagus are closely correlated with aortic pressure, and, furthermore, that measurements made in the esophagus are even more closely correlated to aortic pressure than measurements of $CO_2$ in the stomach. This procedure was advantageous in that the procedure's invasiveness was reduced and $CO_2$ generated by digestive fluids in the stomach did not affect measurements since the esophageal sphincter blocks such gas. However, the insertion of the catheter still constituted considerable invasion and thus risk of harm to the patient. Furthermore, extension of the catheter extended past the epiglottis exposed the patient to the risk of regurgitation of stomach contents including stomach acids.

In co-pending U.S. patent application Ser. No. 09/160,224, filed Sep. 24, 1998, and in the corresponding PCT Application No. PCT/US98/20118, filed Sep. 25, 1998, the present inventors described a less invasive method for assessing impairment of blood circulation in a patient, such as that in perfusion failure, by measurement of $PCO_2$ in the upper digestive and/or respiratory tract of a patient. As explained in the aforementioned U.S. and PCT applications, that method involves introduction of a carbon dioxide sensor into the upper digestive and/or upper respiratory tract of a patient, without passing the sensor down through or beyond the patient's epiglottis. The carbon dioxide sensor is placed adjacent a mucosal surface within the upper digestive and/or respiratory tract, e.g., within a patient's mouth, inside a patient's nose, or at a site along the wall of the esophagus.

Patients who require mechanical ventilatory support pose special problems in measurement of $PCO_2$ using the aforementioned methods. By "mechanical ventilatory support" is meant an apparatus that supports the ventilatory function of the respiratory and improves oxygenation by delivering high oxygen content gas into the endotracheal region of a patient. The apparatus is generally termed a "breathing tube" or "endotracheal tube" ("ETT"). Respiratory failure is the primary indication for use of such respiratory support systems, including hypoxemic respiratory failure, as may result from pulmonary conditions such as pneumonia, pulmonary edema, pulmonary hemorrhage and respiratory distress syndrome, and hypercarbic respiratory failure, such as may be associated with disease states causing inadequate alveolar ventilation to meet metabolic demands. Respiratory support systems are also necessary during many surgical procedures. Mechanical ventilation support systems are known in the art and described, for example, in U.S. Pat. No. 4,502,482 to DeLuccia, deceased et al., U.S. Pat. No. 5,005,573 to Buchanan, U.S. Pat. No. 5,452,715 to Boussignac et al., U.S. Pat. No. 5,606,968 to Mang, U.S. Pat. No. 5,765,559 to Kim, U.S. Pat. No. 5,791,338 to Merchant et al., U.S. Pat. No. 5,803,898 to Bashour, and U.S. Pat. No. 5,806,516 to Beattie.

For seriously ill patients who require mechanical ventilatory support and are thus already burdened with an endotracheal intubation system, introduction of an additional system for $PCO_2$ measurement—such as described in U.S. Pat. No. 5,579,763, U.S. Ser. No. 09/160,224 and PCT Application No. PCT/US98/20118—would be logistically difficult and unnecessary if the measurement could be determined using the existing endotracheal system.

There is a accordingly a need in the art for a method to measure perfusion failure and to monitor the effectiveness of methods taken to increase perfusion, e.g., blood infusion or the like, that are well-suited for use in a mechanically ventilated patient.

SUMMARY OF THE INVENTION

Methods and devices are provided for assessing impairment of blood circulation in a patient, such as that in perfusion failure, by measurement of $PCO_2$ (partial pressure of carbon dioxide) within the lower respiratory tract of the patient. The method comprises introducing a carbon dioxide sensor into the lower respiratory tract of a patient, at a region within the trachea (e.g., below the larnyx and above the bronchi). The carbon dioxide sensor is attached to and/or physically incorporated within an endotracheal breathing tube. Before the work of the present inventors, it was believed that increases in partial pressure of carbon dioxide during perfusion failure were localized phenomena; however, applicants have discovered that increases in tissue $CO_2$ occur throughout the body during perfusion failure, and that such increases in tissue $CO_2$ can be measured at an endotracheal site using the device and method of the invention.

As the invention involves a carbon dioxide sensor appended to an endotracheal breathing tube, the invasiveness involved in introducing the carbon dioxide sensor into the endotracheal area of the patient is no greater than that involved in the insertion of the breathing tube per se. The sensor may be incorporated into any appropriate portion of the endotracheal tube, e.g., on a balloon or cuff portion of the endotracheal apparatus, or along the cannula portion of the endotracheal tube, so long as the sensor is suitably positioned along the tracheal wall for $PCO_2$ measurement. Preferably, the sensor is an optical $CO_2$ sensor. The output of the sensor can be detected by a device which electronically converts the sensor output to provide a $CO_2$ concentration value. The device can further sense the rate of change of $CO_2$ concentration with time to indicate the patient's condition.

Accordingly, in one aspect the invention features a device for assessing perfusion failure in a patient in need of mechanical ventilation, wherein the device is composed of: a mechanical ventilation support system that includes an endotracheal breathing tube provided with a carbon dioxide sensor means for detecting the partial pressure of carbon dioxide ($PCO_2$) along the interior wall of the patient's trachea; and an indicating means operably connected to the sensor means for indicating the degree of perfusion failure of the patient associated with the detected partial pressure of carbon dioxide.

In another aspect the invention features a method for assessing perfusion failure of a patient requiring mechanical ventilation, the method involving the steps of introducing an endotracheal breathing tube into the trachea of the patient as part of a mechanical ventilation support system, wherein the endotracheal breathing tube provided with a carbon dioxide sensor means for detecting the partial pressure of carbon dioxide ($PCO_2$) along the interior wall of the trachea; using the carbon dioxide sensor means to measure the partial pressure of carbon dioxide within the patient's trachea, along the sidewall thereof; and relaying the partial pressure of carbon dioxide so measured to an indicating means that displays the measured $PCO_2$ value, which in turn correlates to the degree of perfusion failure in the patient. A partial pressure of carbon dioxide within the patient's trachea that is substantially greater than a normal partial pressure of carbon dioxide is indicative of perfusion failure in the patient, as is a partial pressure of carbon dioxide within the patient's trachea that increases over time.

One advantage of the invention is that perfusion can be assessed in a patient in a manner that is no more invasive than introducing an endotracheal breathing tube into the patient's trachea, as the perfusion assessment means is incorporated within such a breathing tube. Thus, the invention is advantageous in that it involves minimal additional discomfort or risk of harm to the patient.

Another advantage of the invention is that perfusion can be readily assessed in a patient suffering from perfusion failure associated with any of a variety of causes, including, but not limited to physical trauma, infection, hypothermia, cardiogenic shock (e.g., acute myocardial infarction, aneurysm, or arrhythmia), obstructive shock (e.g., pulmonary embolism), hypovolemic shock (e.g., due to hemorrhage or fluid depletion), and distributive shock (e.g., due to sepsis, exposure to toxins, or anaphylaxis). The invention is readily adapted for assessment of perfusion failure through $PCO_2$ measurement in connection with any situation in which a patient is placed on a mechanical ventilation device or is otherwise subjected to endotracheal intubation (e.g., newborns or premature newborns, patients undergoing surgery requiring general anesthesia, etc.) The sensitivity of the methods and devices of the invention further allow for assessment of perfusion across a wide range of perfusion failure severity, thereby providing a means to accurately monitor the patient's condition.

Still another advantage of the invention is that the devices and methods can be readily adapted for use in alert, semi-conscious, or unconscious patients, and can be further adapted for accurate assessment of perfusion in a patient for a period lasting for only minutes to hours or days.

The novel features of the invention are set forth with particularity in the appended claims. The invention will be best understood from the following description when read in conjunction with the accompanying drawings.

DETAILED DESCRIPTION OF THE INVENTION

Figure 1:
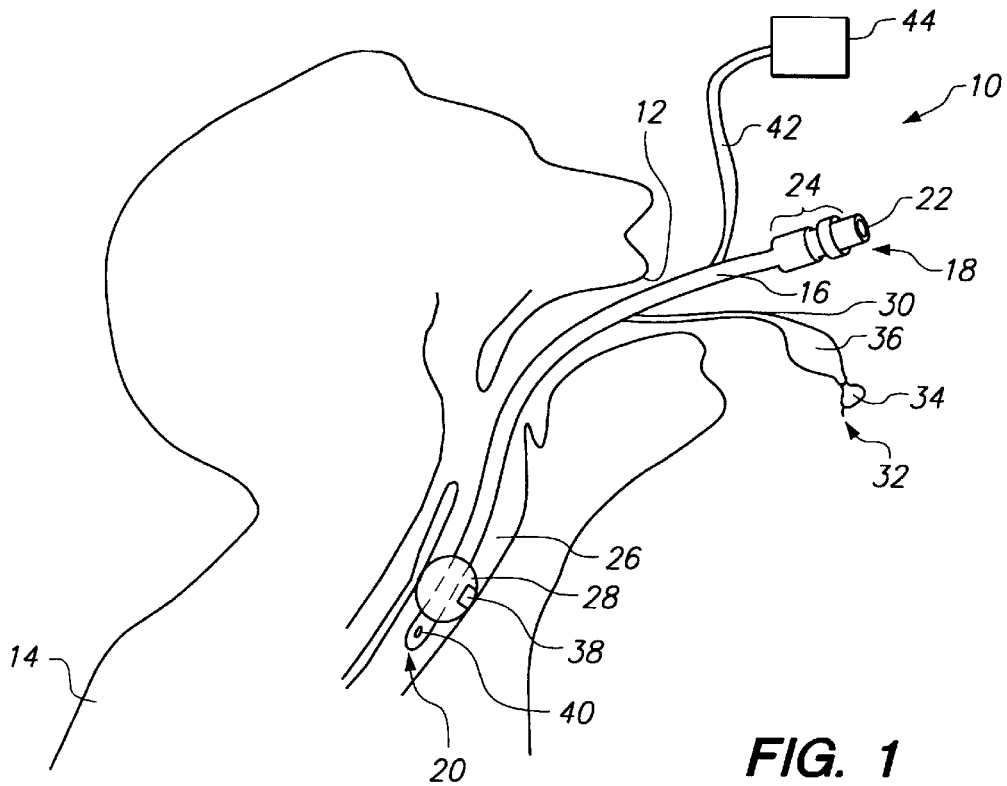
FIG. 1 is a pictorial diagram showing the positioning of the perfusion assessing system of the invention within a patient's trachea.

DEFINITIONS AND NOMENCLATURE:

Before the present devices and methods are disclosed and described, it is to be understood that this invention is not limited to sensor designs, measurement techniques, or the like, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise.

The term "perfusion failure" as used herein is meant a reduction in blood flow associated with maldistribution of blood through the circulatory system and a reduction in blood flow to a less critical tissue and/or organ relative to blood flow in vital (critical) tissues and organs (e.g., the brain and heart). The term "perfusion failure" is clinically also termed "circulatory shock." In general, "perfusion failure" is meant to encompass reduction in blood flow associated with an increase in $PCO_2$ significantly above $PCO_2$ associated with normal perfusion.

The term "measurement" as used herein refers to a single measurement or a series of measurements made over time, and which may be taken continuously or intermittently (e.g., at selected time intervals).

The term "carbon dioxide sensor" is used interchangeably herein with the terms "$CO_2$ sensor" and "$PCO_2$" sensor to refer to sensors for measuring the partial pressure of carbon dioxide.

The term "endotracheal intubation" as used herein generally means the insertion of a tube into the trachea through the nose, mouth, or via a tracheostomy (e.g., for the purpose of maintaining an airway or preventing aspiration of food into the airway).

The term "mucosal surface" as used herein refers to a surface of a mucous membrane containing or associated with mucus secreting glands, and which lines body passages, tubular structures, and organs. The mucosal surface of interest herein is the sidewall of a patient's trachea.

The term "adjacent" as used herein (e.g., "adjacent the mucosal surface") means near or against, e.g., at a distance from the mucosal surface that allows acceptably accurate measurement of the partial pressure of carbon dioxide by a $PCO_2$ sensor. In general, it is preferable that the $PCO_2$ sensor actually come into contact with the sidewall of the patient's trachea, but it is sufficient that the sensor be "adjacent" thereto as just defined.

The term "patient" as used herein means a mammalian subject, preferably a human subject, that has, is suspected of having, or is or may be susceptible to a condition associated with low blood flow, and thus perfusion failure.

The present invention thus provides a method and device for assessing perfusion failure in a patient requiring mechanical ventilation. The invention involves monitoring $PCO_2$ within the trachea, and/or the rate of change of $PCO_2$ within the trachea, as high endotracheal $PCO_2$ values and increasing endotracheal $PCO_2$ values are associated with perfusion failure, wherein the $PCO_2$ monitoring is conducted with an endotracheal breathing tube having a $PCO_2$ sensor incorporated therein or attached thereto.

THE DEVICE AND METHOD OF THE INVENTION:

FIG. 1 illustrates a preferred device of the invention, showing an endotracheal tube represented generally as 10 inserted through the mouth 12 of patient 14. The tube can, however, be inserted through the patient's nose, or through a tracheostomy. The tube includes a cannula 16 having a proximal end 18 and a distal end 20, wherein the proximal end is provided with a terminal orifice 22 and a connector 24 for connection to a breathable air supply for introduction of gases to the patient's lungs. The distal end 20 of the cannula is shown placed within trachea 26 of the patient. The endotracheal tube is provided with a sealing means for maintaining an air seal between the cannula and the trachea. Preferably, the tube is a conventional "cuffed" tube having as the sealing means an inflatable cuff shown at 28 in an inflated state as it would be during a surgical procedure. Both the cuff and the cannula are preferably generally constructed of radio-opaque bio-compatible polyvinyl chloride, but as will be appreciated by those skilled in the art other suitable materials may be substituted therefor. The cuff 28 is inflated by introduction of air into cuff inflation line 30 by attachment of a syringe or the like to the open terminus 32 of the cuff inflation line. The flow of air that is introduced into open terminus 32 of the cuff inflation line 30 is controlled by valve 34, with inflation of pilot balloon 36 indicating inflation of the cuff. The $PCO_2$ sensor 38 is shown attached to the exterior of cuff 28 and lying against the inside wall of the patient's trachea, but as will be appreciated by those skilled in the art and as described elsewhere herein, the $PCO_2$ sensor is not necessarily positioned on cuff 28. It is merely required that the $PCO_2$ sensor be incorporated within or attached to endotracheal tube 10 in such a way as to be positioned adjacent to and preferably contact the inner wall of the patient's trachea 26.

To properly place the device so that $PCO_2$ measurements can be made within the patient's trachea, the endotracheal tube 10 is inserted into the mouth or nose of the patient, or through a tracheostomy, extended through the pharynx and larynx, and into the trachea 26. The tube 10 must be sufficiently long so that the proximal end 18 of the cannula and the terminus 32 of the cuff inflation line 30 extend beyond the patient's mouth while the distal end 20 of the cannula is in the patient's trachea 26. After insertion of the endotracheal tube 10, the proximal end 18 of the cannula is attached through terminal orifice 22 and connector 24 to a supply of breathable air (not shown). A positive pressure of air in the lungs is maintained by pumping air from the breathable air supply by introduction of air into terminal orifice 22, through cannula 16 and into the patient's trachea 26 through aperture 40 present at the distal end of the cannula. Prior to introducing air in this way, cuff 28 is inflated by introducing air into the cuff inflation line 30 by a syringe or the like. When the cuff is inflated, the cuff 28 conforms to the natural shape of the trachea while providing a seal with the trachea wall. Inflation of the cuff also forces $PCO_2$ sensor against the trachea wall, as desired for assessment of perfusion failure using the method of this invention.

In accordance with the present invention, applicants find that a precise assessment of perfusion failure in a patient requiring mechanical ventilation can be obtained by measuring $PCO_2$ in the trachea using a device as just described. Since carbon dioxide can readily pass through mucosal surfaces, $CO_2$ generated by metabolic activity occurring in tissue below the mucosal surface that is not carried away by blood flow readily migrates through the mucosal surface. Placement of a $PCO_2$ sensor adjacent the interior wall of the trachea thus provides a very good quantification of perfusion failure at all times, including the most critical minutes after the onset of perfusion failure when treatment is likely to be most effective.

As illustrated in FIG. 1, the $PCO_2$ sensor is operably connected through a flexible cable or catheter 42 to a test instrument 44 including an indicator means that typically indicates the partial pressure of $CO_2$ in millimeters of mercury (mmHg), which provides an indicia of a degree of perfusion failure.

The $CO_2$ sensor may be any $CO_2$ sensor suitable for detection of $PCO_2$ in the manner described herein. Typical $CO_2$ sensors used in the examples herein operate by detecting a change in pH in the sensor environment. Specifically, such sensors have a membrane that is permeable to $CO_2$, and that separates a sodium bicarbonate or carbonic acid ($HCO_3$) solution from the environment. A pH sensor in the device measures the pH of the sodium bicarbonate solution. Two exemplary $CO_2$ sensors of this type are manufactured by Microelectrode, Inc. and Nihon Kohden (ISFET $PCO_2$ sensor).

Alternatively, the $CO_2$ sensor is an optical $PCO_2$ sensor. Structures, properties, functions, and operational details of fiber optic chemical sensors can be found in U.S. Pat. Nos. 4,577,109; 4,785,814; and 4,842,783, as well as in Seitz, "Chemical Sensors Based on Fiber Optics," *Anal. Chem.* 56(1):16A–34A (1984). Fiber optic sensors for monitoring $CO_2$ that may be suitable for use in the present invention include, but are not limited to, those described in U.S. Pat. Nos. 4,892,383; 4,919,891; 5,006,314; 5.098,659; 5,280, 548; and 5,330,718. Other exemplary fiber optic $CO_2$ sensors are described in Peterson et al. "Fiber Optic Sensors for Biomedical Applications," *Science* 224(4645):123–127 (1984) and Vurek et al. "A Fiber Optic $PCO_2$ Sensor," *Annals Biomed. Engineer.* 11:499–510 (1983).

A suitable optical $CO_2$ sensor is described in U.S. Pat. No. 5,714,121 ('121) to Alderete et al., of common assignment herewith, which pertains to an optical $CO_2$ sensor and method of manufacture thereof; a preferred sensor system and method of using the aforementioned optical $CO_2$ sensor is described in U.S. Pat. No. 5,672,515 ('515) to Furlong, also of common assignment herewith. In general, the sensor of the '121 patent is composed of a single optical fiber having a distal tip and a proximal region for communication with a means for receiving a signal from the distal tip. Light of a predetermined wavelength is directed through the optical fiber towards the distal tip, and emitted fluorescent light returns along the fiber to be detected and converted to a $CO_2$ concentration value. A capsule, composed of a $CO_2$-permeable silicone material, is arranged over the distal tip at a predetermined position. The capsule contains an indicator solution having a suitable pH-sensitive indicator component, generally a fluorescent dye, and substantially no air. Examples of fluorescent dyes include without limitation fluorescein, carboxyfluorescein, seminaphthorhodafluor, seminaphthofluorescein, naphthofluorescein, 8-hydroxypyrene 1,3,6-trisulfonic acid, trisodium salt ("HPTS") and dichlorofluorescein, with HPTS particularly preferred. A sealing means provides a liquid-tight seal and affixes the capsule onto the distal tip.

Optical $CO_2$ sensors are generally used by contacting the distal end of the sensor with a mucosal surface as described herein. Light of a predetermined wavelength is directed from an external source, through the optical fiber, impinging distally on the encapsulated indicator composition. The intensity of the emitted fluorescent light returning along the fiber is directly related to the concentration of $CO_2$ in the sample, as a result of the pH-sensitive indicator material present at the fiber tip (i.e., the pH of the indicator solution is directly related to $CO_2$ concentration, as a result of carbonic acid formation). The emitted light is carried by the optical fiber to a device where it is detected and converted electronically to a $CO_2$ concentration value. The sensor may additionally have a reference dye present in the indicator composition. The intensity of the light emitted from the reference dye may be used to compensate, via rationing, the signal obtained from the indicator. A more preferred system for determining $PCO_2$ is described in the '515 patent, directed to a simultaneous dual excitation/single emission fluorescent sensing method, wherein light of two different wavelengths is used to excite a single fluorescent indicator species, with one of the two wavelengths at the isosbestic point. The two fluorescence emission signals that result are ratioed to provide the desired measurement.

Figure 2:
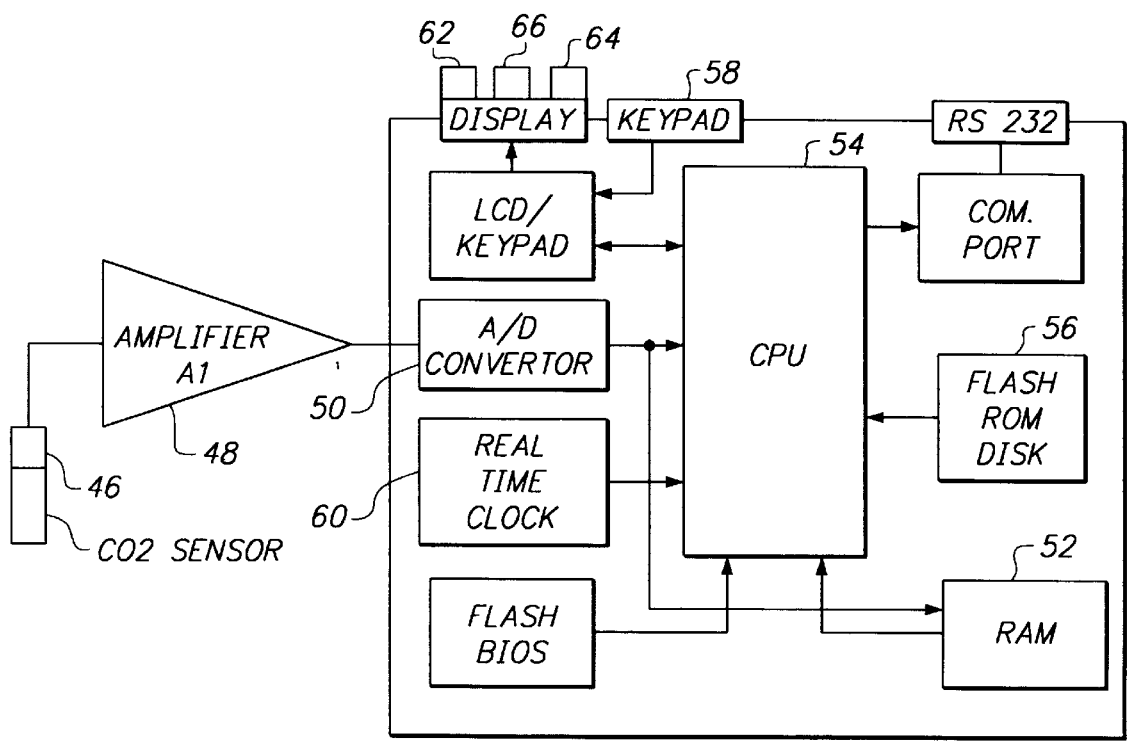
FIG. 2 is an electrical block diagram of one embodiment of a circuit for processing output data from a $PCO_2$ sensor located within a patient's trachea.

The data provided by the $CO_2$ sensor may be acquired and analyzed by any appropriate means available. For example, FIG. 2 shows data acquisition circuitry that can be used to facilitate $CO_2$ data analysis. The circuit includes preamplifier 46 and amplifier 48, which deliver signals representing the $CO_2$ level to an A/D converter 50. The converter output is delivered to a memory 52 which stores the values and delivers them to a CPU, or central processing unit 54. Software for instructing the CPU to operate on the data, is contained in a memory disk 56. Pertinent information such as characteristics of the patient can be inputted through a keyboard 58. $CO_2$ levels are delivered to the CPU at a rate of five samples per second. The CPU uses this data and the elapsed time from a clock 60 to deliver signals indicating the perfusion state of the patient. Alternatively, the signals displayed may simply indicate the $PCO_2$ value, from which one skilled in the art can evaluate the degree of perfusion failure. When the signals represent the output of a $CO_2$ data analysis program, and thus the degree of perfusion failure, various types of indicator means can be used. For example, if the patient's condition is poor, a red light 62 may be illuminated, if the patient's condition is stable a green light 64 may be illuminated, and if the patient's condition is guarded a yellow light 66 may be illuminated. This simplistic output is useful for moderately skilled persons such as medics in the armed forces and paramedics on ambulances. An indication of the patient's condition enables the health worker to determine whether or not the patient should be rushed to a treatment center and/or whether certain steps should be taken to enhance perfusion such as repeated depression of the chest.

The software that controls the CPU can be programmed to determine which of the three signals (red light, green light or yellow light) should be displayed. In general, a particular high level of carbon dioxide Z, as well as a low level of carbon dioxide Y, are established. These high and low levels may be, for example, a Z value of 80 mm Hg and a Y value of 50 mm Hg. In addition, the CPU continually determines the rate of increase or decrease of $PCO_2$. A rate of $PCO_2$ increase of more than 20 mmHg/hr. indicates a high degree of perfusion failure, while, in comparison, a rate of $PCO_2$ increase less than 20 mmHg/hr. connotes a lower degree of perfusion failure. If the $PCO_2$ level is decreasing, or negative, the patient is viewed as stable.

Patients having a $PCO_2$ greater than Z may be assigned to a first patient category, wherein, if the rate of change of $PCO_2$ in these first category patients is zero or positive, then the condition of the patient is assessed as being poor and the red light is energized. If $PCO_2$ is decreasing, then the yellow light is energized to indicate that the patient is in a guarded state. If the initial $PCO_2$ measurement is between the two levels Z and Y, then the patient is assigned to a second patient category. The condition of a second category patient is guarded, and thus the yellow light energized, unless the $PCO_2$ level is increasing at more than 20 mm Hg/hr., in which case the red light is energized. For a third category patient, the carbon dioxide level is less than Y, and the patient is deemed to be in a stable condition. If there is a considerable change in carbon dioxide, e.g., the $PCO_2$ level increases at a rate of more than 20 mm Hg/hr. or decreases at a certain rate such as 10 mmHg/hr. Where the $CO_2$ level is less than Y, a considerable change in $CO_2$ level may indicate that the patient suffers from a condition associated with abnormally high blood flow.

Figure 3:
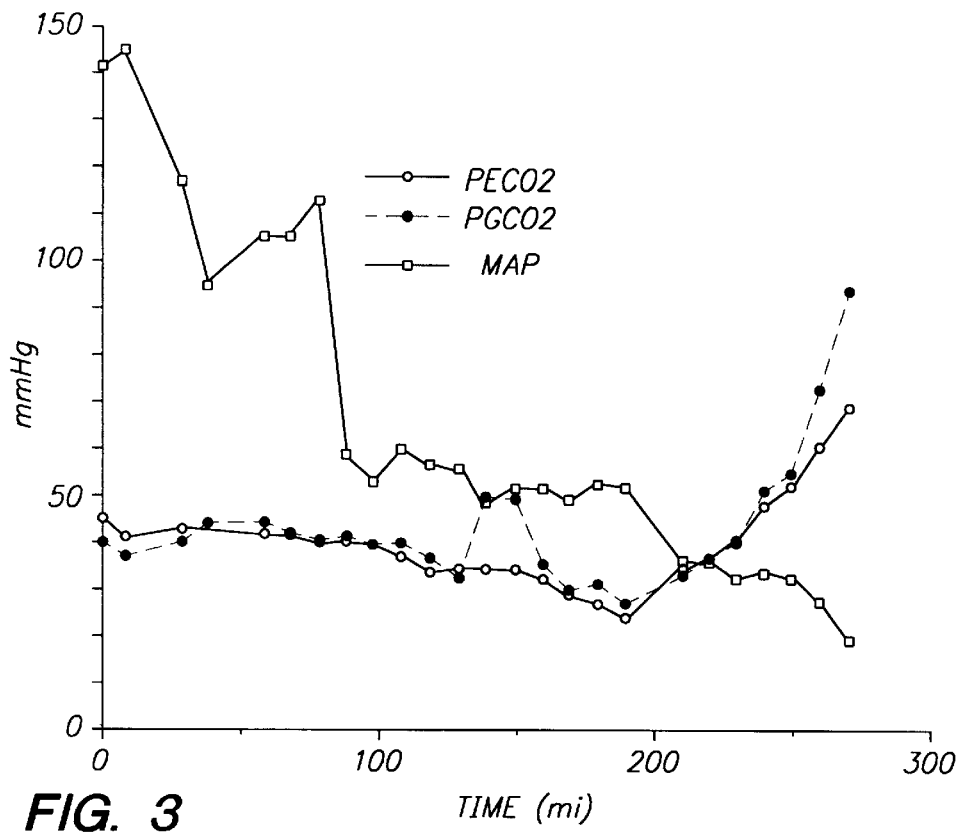
FIG. 3 is a graph showing the results of a first feasibility study conducted with rats using endotracheal tubes modified to accommodate a $PCO_2$ sensor; in the graph, "$P_ECO_2$" represents endotracheal $PCO_2$ (in mm Hg), "$P_GCO_2$" represents gastric wall $PCO_2$ (in mm Hg), and "MAP" represents the mean arterial pressure (again, in mm Hg).
Figure 4:
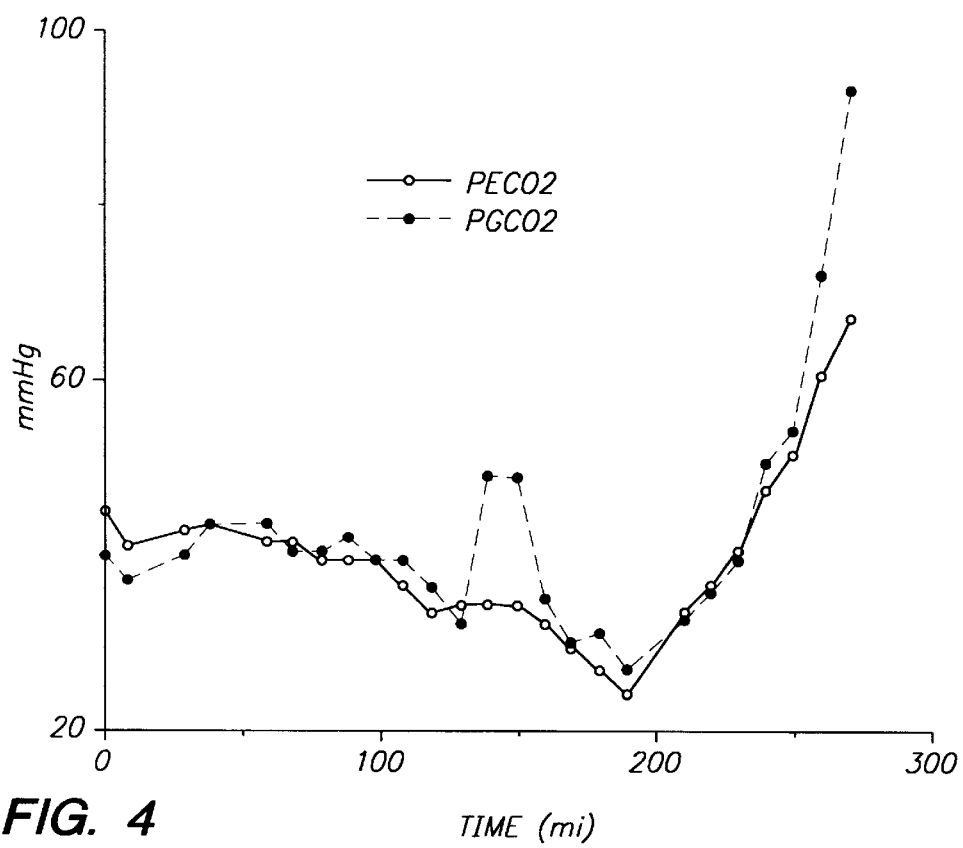
FIG. 4 is a graph showing the results of a second feasibility study conducted with rats using endotracheal tubes modified to accommodate a $PCO_2$ sensor, with abbreviations and units as set forth above with respect to FIG. 3.
Figure 5:
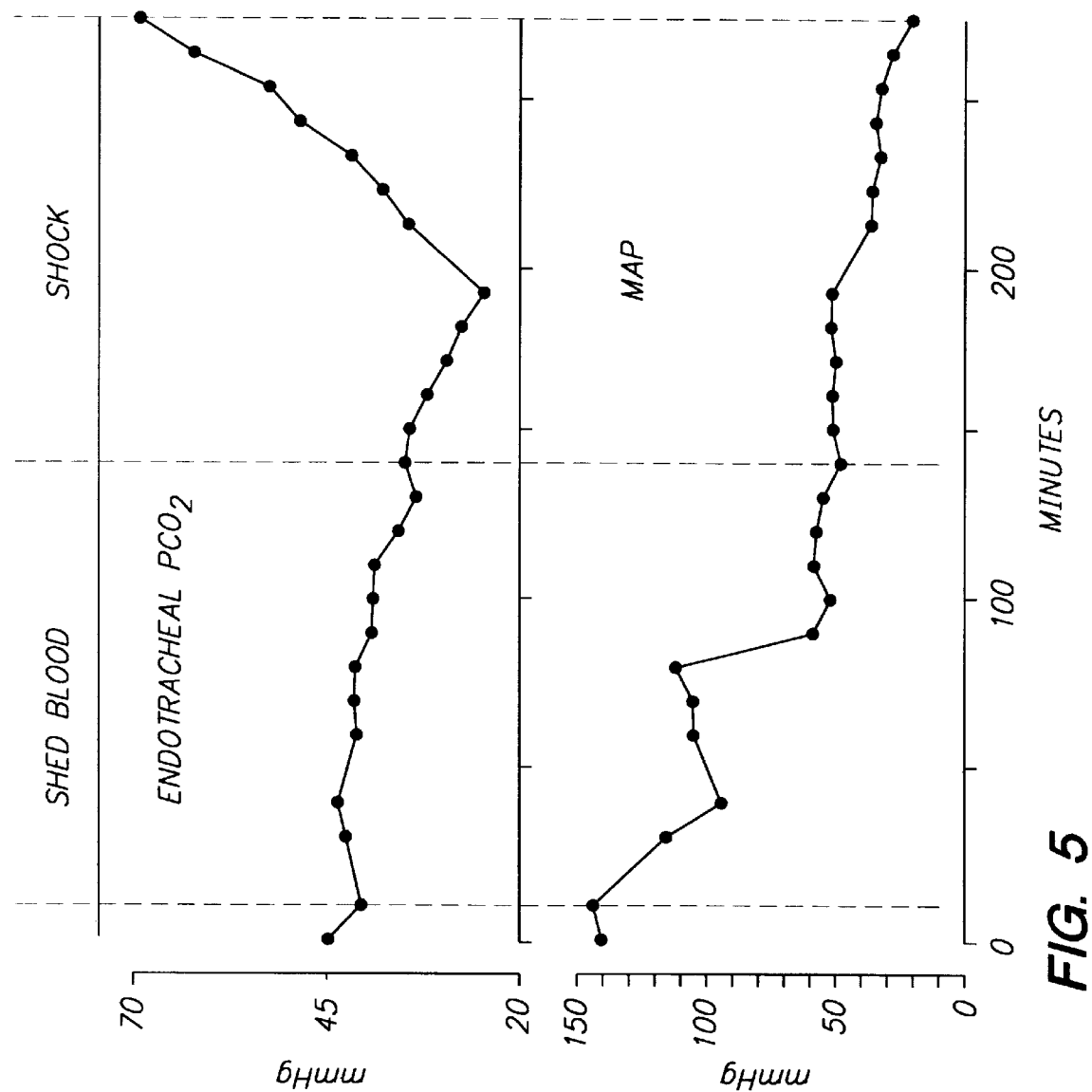
FIG. 5 is a graph showing the endotracheal $PCO_2$ (mm Hg; upper panel) in relationship to the MAP (again, in mm Hg; lower panel), during bleeding, in a test animal.

The correlation of perfusion failure with high endotracheal $PCO_2$ levels and/or increasing endotracheal $PCO_2$ levels, as well as the correlation of perfusion recovery and low or decreasing endotracheal $PCO_2$ levels, were tested in an animal (rat) model that simulates a sudden loss or shedding of blood, such as might be caused by a gunshot wound or other severe wound. Perfusion recovery was simulated by subsequently reperfasing the animal with a blood infusion. The results are shown in graph form in FIGS. 3, 4 and 5. As indicated on the aforementioned figures, "$P_ECO_2$" represents endotracheal $PCO_2$ (in mm Hg), "$P_GCO_2$" represents gastric wall $PCO_2$ (in mm Hg), and "MAP" represents the mean arterial pressure (again, in mm Hg). All $PCO_2$ measurements were made using sensors manufactured by Microelectrode, Inc., as discussed earlier herein.

At the beginning of the test (time=0 in the graphs of FIGS. 3–5), considerable blood was drawn from an animal that was previously in good health, the blood being drawn within a period of a few minutes. Initially, between approximately 10 and 50 minutes, as may be seen in FIGS. 3 and 5, mean arterial pressure ("MAP") dropped rapidly, about 30%. In the subsequent period, from about 50 minutes to about 120 minutes, the mean arterial pressure remained about 40% below normal. After 120 minutes, the mean arterial pressure continued to drop; see FIGS. 3 and 5. Correspondingly, the partial pressure of carbon dioxide, measured both in the trachea and along the gastric wall, remained stable and ultimately increased significantly as mean arterial pressure continued to drop. These data show that an increase in $PCO_2$, whether measured in the trachea or along the gastric wall, is inversely correlated with mean arterial pressure during perfusion failure.

The results in the animal model can be extrapolated to represent a human subject suffering perfusion failure. The present invention takes advantage of these phenomena to provide methods and devices to assist a physician or other health care provider in the diagnosis and treatment of a patient having or susceptible to a condition associated with perfusion failure.

For example, although assistance from a paramedic or other person may be available shortly after the initial primary insult, it may take thirty minutes or more for the patient to reach a hospital. During that time, i.e., during transport, the patient may be intubated, and the method and apparatus for measuring $PCO_2$ according to the present invention allows the physician or other healthcare provider to readily detect the level of $PCO_2$ relative to normal, as well as the rate of change of $PCO_2$. A rapid increase in $PCO_2$ suggests that the patient has suffered a loss of blood within the last hour or so, while a high level of $PCO_2$ indicates the patient presently suffers from a low level of aortic pressure and perfusion failure. In this manner the invention can be used to assess the patient's condition, allowing for appropriate and rapid selection of an appropriate therapy.

Thus, the invention provides a method and device for assessing perfusion failure in patients requiring mechanical ventilation in the form of an endotracheal breathing tube. The method may be performed rapidly, with minimal equipment other than that required for the mechanical ventilation system. The invention is useful in a variety of contexts in which a patient requires mechanical ventilation, e.g., patients who have suffered respiratory failure, patients undergoing surgery requiring general anaesthesia, and the like, and wherein ventilation may be effected in one of any number of modes, e.g., assist control mode ventilation ("ACMV"), synchronized intermittent mandatory ventilation ("SIMV"), continuous positive airway pressure ("CPAP"), pressure-control ventilation ("PCV"), pressure-support ventilation ("PSV"), proportional assist ventilation ("PAV"), or the like. The invention is also useful in the treatment and monitoring of newborn infants, as on the order of 1–2% of newborns require some sort of intensive care immediately following birth. For example, premature babies frequently require cardiorespiratory support, while mature babies, also, can suffer from birth asphyxia, sepsis or hypoxia, possibly leading to pulmonary hypertension. Newborns requiring mechanical ventilation in these and other cases will benefit from the device and method of the invention, in that a rapid and accurate assessment of perfusion failure can be made during mechanical ventilatory support.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

All patents, patent documents, journal articles and other references cited herein are hereby incorporated by reference in their entireties.

What is claimed is:

1. A device for assessing the degree of perfusion failure in a patient requiring mechanical ventilatory support, the device comprising:

an endotracheal breathing tube comprised of a cannula for carrying air from an air supply pump to the lungs of a patient, the cannula having a proximal end for receiving air from the air supply pump and a distal end having an aperture for releasing air into the patient's trachea; and carbon dioxide sensor means for detecting the partial pressure of carbon dioxide, with the patient's trachea the sensor means physically connected to the endotracheal breathing tube in a manner that allows for $PCO_2$ measurement along the sidewall of the patient's trachea.

2. The device of claim 1, further comprising indicator means for indicating the detected partial pressure of carbon dioxide in the patient's trachea, the indicator means operably connected to the carbon dioxide sensor.

3. The device of claim 2, wherein the carbon dioxide sensor comprises a fiber optic $PCO_2$ sensor.

4. The device of claim 1, wherein the carbon dioxide sensor comprises a fiber optic $PCO_2$ sensor.

5. The device of claim 1, further including a means for sealing the cannula within the patient's trachea.

6. The device of claim 5, wherein the sealing means comprises an inflatable cuff at the distal end of the cannula.

7. The device of claim 6, further including a means for inflating said cuff.

8. The device of claim 6, wherein the carbon dioxide sensor means is affixed to the exterior of the inflatable cuff, whereby upon inflation thereof the sensor means is forcibly positioned against the sidewall of the patient's trachea.

9. A device for assessing the degree of perfusion failure in a patient requiring mechanical ventilatory support, comprising:

an endotracheal breathing tube comprised of a cannula for carrying air from an air supply pump to the lungs of a patient, the cannula having a proximal end for receiving air from the air supply pump and a distal end having an aperture for releasing air into the patient's trachea;

an optical carbon dioxide sensor for detecting the partial pressure of carbon dioxide, within the patient's trachea the sensor physically connected to the endotracheal breathing tube in a manner that allows for $PCO_2$ measurement along the sidewall of the patient's trachea, wherein the sensor is comprised of an optical fiber means provided with a fluorescent indicator composition;

means for irradiating the indicator composition with light of a predetermined wavelength which causes the indicator composition to emit fluorescent light having an intensity proportional to the $PCO_2$ value in the region surrounding the sensor; and means for converting the intensity of the emitted fluorescent light to a value indicative of $PCO_2$.

10. The device of claim 9, wherein the irradiating means is capable of irradiating the indicator composition with light of two different wavelengths, and wherein one of the wavelengths is at the isosbestic point.

11. The device of claim 9, wherein the indicator composition is contained within a capsule arranged over the distal tip of the optical fiber means.

12. A method for assessing the degree of perfusion failure in a patient requiring mechanical ventilatory support, comprising:

(a) providing an endotracheal breathing tube comprised of a cannula for carrying air from an air supply pump to the lungs of the patient, the cannula having a proximal end for receiving air from the air supply pump and a distal end having an aperture for releasing air into the patient's trachea, the endotracheal breathing tube further including, at the distal end of the cannula, a carbon dioxide sensor means for detecting the partial pressure of carbon dioxide along the sidewall of the patient's trachea;

(b) introducing the distal end of the endotracheal breathing tube into the trachea of the patient so that the carbon dioxide sensor means is positioned against the sidewall thereof; and (c) detecting the partial pressure of carbon dioxide in the patient's trachea.

13. The method of claim 12, further including determining the degree of perfusion failure in the patient from the detected partial pressure of carbon dioxide in the patient's trachea.

14. The method of claim 12, wherein step (c) is repeated so that the rate of change of the partial pressure of carbon dioxide in the patient's trachea can be determined.

15. The method of claim 14, further including determining the degree of perfusion failure in the patient from the rate of change of the detected partial pressure of carbon dioxide in the patient's trachea.

16. The method of claim 12, further including introducing air from an air supply pump through the cannula and into the patient's trachea after step (b) and prior to or during step (c).

17. The method of claim 16, wherein the endotracheal breathing tube further includes a means for sealing the cannula within the patient's trachea.

18. The method of claim 17, wherein the sealing means comprises an inflatable cuff at the distal end of the cannula.

19. The method of claim 18, further comprising inflating said cuff prior to introduction of air into the patient's lungs.

20. The method of claim 19, wherein the carbon dioxide sensor means is affixed to the exterior of the inflatable cuff, whereby upon inflation thereof the sensor means is forcibly positioned against the sidewall of the patient's trachea.

21. The method of claim 18, wherein the carbon dioxide sensor means is affixed to the exterior of the inflatable cuff, whereby upon inflation thereof the sensor means is forcibly positioned against the sidewall of the patient's trachea.

22. The method of claim 12, wherein the carbon dioxide sensor means comprises a fiber optic $PCO_2$ sensor.

23. The method of claim 12, wherein the endotracheal breathing tube further includes a means for sealing the cannula within the patient's trachea.

24. The method of claim 23, wherein the sealing means comprises an inflatable cuff at the distal end of the cannula.

25. The method of claim 24, wherein the carbon dioxide sensor means is affixed to the exterior of the inflatable cuff, whereby upon inflation thereof the sensor means is forcibly positioned against the sidewall of the patient's trachea.

26. The method of claim 12, wherein the patient requiring mechanical ventilatory support is a surgery patient requiring general anesthesia.

27. The method of claim 12, wherein the patient requiring mechanical ventilatory support is a neonate.

28. A method for assessing the degree of perfusion failure in a patient requiring mechanical ventilatory support, comprising:

(a) providing an endotracheal breathing tube comprised of a cannula for carrying air from an air supply pump to the lungs of the patient, the cannula having a proximal end for receiving air from the air supply pump and a distal end having an aperture for releasing air into the patient's trachea, the endotracheal breathing tube further including, at the distal end of the cannula, an optical carbon dioxide sensor for detecting the partial pressure of carbon dioxide along the sidewall of the patient's trachea, wherein the sensor is comprised of an optical fiber means provided with a fluorescent indicator composition;

(b) positioning the endotracheal breathing tube so that the optical carbon dioxide sensor contacts the sidewall of the patient's trachea;

(c) irradiating the indicator composition with light of a predetermined wavelength so as to cause the indicator composition to emit fluorescent light having an intensity proportional to the $PCO_2$ value in the region surrounding the sensor means; and (d) converting the intensity of the emitted fluorescent light to a value indicative of $PCO_2$.

29. The method of claim 28, further including determining the degree of perfusion failure in the patient from the detected partial pressure of carbon dioxide in the patient's trachea.

30. The method of claim 28, wherein step (c) is repeated so that the rate of change of the partial pressure of carbon dioxide in the patient's trachea can be determined.

31. The method of claim 30, further including determining the degree of perfusion failure in the patient from the rate of change of the detected partial pressure of carbon dioxide in the patient's trachea.

32. The method of claim 28, further including introducing air from an air supply pump through the cannula and into the patient's trachea after step (b) and prior to or during step (c).

33. The method of claim 32, wherein the endotracheal breathing tube further includes a means for sealing the cannula within the patient's trachea.

34. The method of claim 33, wherein the sealing means comprises an inflatable cuff at the distal end of the cannula.

35. The method of claim 34, further comprising inflating said cuff prior to introduction of air into the patient's lungs.

36. The method of claim 35, wherein the carbon dioxide sensor means is affixed to the exterior of the inflatable cuff, whereby upon inflation thereof the sensor means is forcibly positioned against the sidewall of the patient's trachea.

37. The method of claim 34, wherein the carbon dioxide sensor means is affixed to the exterior of the inflatable cuff, whereby upon inflation thereof the sensor means is forcibly positioned against the sidewall of the patient's trachea.

38. The method of claim 28, wherein the carbon dioxide sensor means comprises a fiber optic $PCO_2$ sensor.

39. The method of claim 38, wherein the sealing means comprises an inflatable cuff at the distal end of the cannula.

40. The method of claim 39, wherein the carbon dioxide sensor means is affixed to the exterior of the inflatable cuff, whereby upon inflation thereof the sensor means is forcibly positioned against the sidewall of the patient's trachea.

41. The method of claim 28, wherein the endotracheal breathing tube further includes a means for sealing the cannula within the patient's trachea.

42. The method of claim 28, wherein the patient requiring mechanical ventilatory support is a surgery patient requiring general anesthesia.

43. The method of claim 28, wherein the patient requiring mechanical ventilatory support is a neonate.

* * * * *